United States Patent
Zhang et al.

(10) Patent No.: US 10,119,240 B2
(45) Date of Patent: Nov. 6, 2018

(54) TEST SYSTEM AND TEST METHOD FOR DETECTING CEMENT CONTENT OF CEMENT MIXING PILE BODY IN REAL TIME

(71) Applicant: HOHAI UNIVERSITY, Nanjing, Jiangsu (CN)

(72) Inventors: Fuhai Zhang, Jiangsu (CN); Qing Chen, Jiangsu (CN); Qingsong Zuo, Jiangsu (CN); Saifeng Yuan, Jiangsu (CN)

(73) Assignee: HOHAI UNIVERSITY (CN)

( * ) Notice: Subject to any disclaimer, the term of this patent is extended or adjusted under 35 U.S.C. 154(b) by 105 days.

(21) Appl. No.: 15/518,478

(22) PCT Filed: Jan. 6, 2016

(86) PCT No.: PCT/CN2016/070249
§ 371 (c)(1),
(2) Date: Apr. 11, 2017

(87) PCT Pub. No.: WO2017/067097
PCT Pub. Date: Apr. 27, 2017

(65) Prior Publication Data
US 2018/0023268 A1     Jan. 25, 2018

(30) Foreign Application Priority Data
Oct. 23, 2015   (CN) .......................... 2015 1 0532804

(51) Int. Cl.
*E02D 33/00* (2006.01)
*E02D 5/46* (2006.01)
(Continued)

(52) U.S. Cl.
CPC ............... *E02D 33/00* (2013.01); *E02D 5/46* (2013.01); *G01N 9/26* (2013.01); *G01N 9/36* (2013.01);
(Continued)

(58) Field of Classification Search
CPC ............ G01N 9/00; G01N 9/002; G01N 9/32; G01N 9/20; G01N 7/14; G01N 33/383; G01N 9/02; G01N 3/00; G01N 2203/0092
(Continued)

(56) References Cited

FOREIGN PATENT DOCUMENTS

| CN | 101831909 A | 9/2010 |
| CN | 203008000 U | 6/2013 |

(Continued)

OTHER PUBLICATIONS (English Translation) Feng, Cement mixing pile construction slurry flow real-time control device, Sep. 2010, Hohai University, CN101831909A, pp. 1-11.*

*Primary Examiner* — John Fitzgerald
*Assistant Examiner* — Truong D Phan

(57) ABSTRACT

The present invention discloses a test system and a test method for detecting the cement content of cement stirring pile body in real time at a construction site. The test system specifically includes a cement slurry density measuring apparatus and a cement admixing amount calculating apparatus. The method includes measuring the density of the cement slurry in the cement slurry tank, measuring the cement soil density and inputting measured values to calculate the cement content. The cement slurry density and the cement soil density can be detected in real time, so that the admixing amount of the cement can be detected in real time during the foundation reinforcing process of the underground engineering, convenience and rapidness are achieved, the time period is short, a supervision effect is (Continued)

good, and cheating on workmanship and materials can be effectively avoided.

6 Claims, 3 Drawing Sheets

(51) Int. Cl.
    *G01N 9/36*     (2006.01)
    *G01N 9/26*     (2006.01)
    *G01N 33/38*     (2006.01)

(52) U.S. Cl.
    CPC ....... *G01N 33/383* (2013.01); *E02D 2600/10* (2013.01)

(58) Field of Classification Search
    USPC .......................... 73/32 R, 30.01, 19.08, 803
    See application file for complete search history.

(56) References Cited

FOREIGN PATENT DOCUMENTS

| | | |
|---|---|---|
| CN | 105113499 A | 12/2015 |
| JP | 09143993 A | 6/1997 |

\* cited by examiner

TEST SYSTEM AND TEST METHOD FOR DETECTING CEMENT CONTENT OF CEMENT MIXING PILE BODY IN REAL TIME

FIELD

The present invention relates to a test system and a test method for detecting the cement content at a construction site, and in particular relates to a test system and a test method for detecting the cement content of a cement mixing pile body in real time, which are suitable for detecting the cement admixing amount of a cement mixing pile, a high-pressure jet grouting pile, etc., and belongs to the field of underground engineering.

BACKGROUND

A great number of underground engineering projects such as high building foundation reinforcement, foundation pit excavation, bridge erection, express way roadbed reinforcement, etc. need to be reinforced at a foundation by grouting. In the prior art, the cement slurry at the construction site needs to be brought back to a laboratory to be detected, and a core sample needs to be extracted on site when the cement soil density is detected, so that the detection means is complex, the period is relatively long, and the problem such as the existence of cheating on workmanship and materials is difficult to determine rapidly. For the fact that the construction of the underground engineering has certain concealment, a construction unit may cheat on workmanship and materials for its own benefit when in operation, which brings great safety potential hazard to the infrastructure in China. Therefore, there is an urgent need for a technical means to detect a cement admixing amount in real time at the construction site.

SUMMARY

In order to solve the defects of the prior art, the present invention is directed to a test system and a test method for detecting the cement content of a cement mixing pile body in real time at a construction site.

In order to achieve the above-mentioned objectives, the present invention adopts a technical solution as follows.

The present invention first discloses a test system for detecting the cement content of a cement mixing pile body in real time. The test system specifically includes a cement slurry density measuring apparatus and a cement admixing amount calculating apparatus, wherein the cement slurry density measuring apparatus includes a first electric control center, a measuring wire electrically connected with the first electric control center and a plurality of first pressure sensors; the first electric control center includes a power supply, a switch, a voltmeter, a resistor, a data processing module and a first display module; when the measuring wire perpendicularly drops to contact with the cement slurry liquid surface from the top of the cement slurry tank, the numerical value of the voltmeter changes; the first pressure sensors are arranged at the bottom of the cement slurry tank, and the pressure test data is fed back to the data processing module, and the cement slurry density is calculated and then displayed on the first display module.

The cement admixing amount calculating apparatus includes a second electric control center and a second pressure sensor electrically connected with the second electric control center, where the second pressure sensor is fixed at the end portion of the drill bit, and the drill bit stretches into the pile body to be tested; the second electric control center includes a data acquisition module, a single chip microprocessor, a second display module and an input module, and when data acquired by the second sensor is fed back to the data acquisition module, the cement soil density is calculated by the single chip microprocessor and then displayed on the second display module; and the cement slurry density, the cement soil density, water cement ratio and soil density are input into the input module, and then the cement content is calculated by the single chip microprocessor and displayed on the second display module.

Preferably, the number of the aforementioned first pressure sensors is 2, 4 or 6, and the first pressure sensors are uniformly distributed on the bottom wall of the cement slurry tank; and the measurement precision can be improved by means of calculating an average value.

Further, the end portion of the aforementioned measuring wire is provided with a gravity block, thus it can ensure the vertical dropping of the wire from the top of the cement slurry tank so that to ensure the reliability of the test results.

Furthermore, the present invention also discloses a test method for detecting the cement content of a cement mixing pile body in real time using the foregoing test system, which specifically includes the following steps:

S1. The density of the cement slurry in the cement slurry tank is measured: the switch of the first electric control center is closed; the measuring wire is vertically dropped from the top of the cement slurry tank; the measuring wire contacts with the liquid surface of the cement slurry when the reading of the voltmeter changes; the length h of the measuring wire and the height H of the cement slurry tank are measured; the return value P of each first pressure sensor is also recorded; and the cement slurry density is calculated by the data processing module according to the formula $\rho_{cement\ slurry} = P/g(H-h)$, wherein $g = 9.8\ g/cm^3$;

S2. Cement soil density is measured: a stress measuring signal is transmitted by the second electric control center; data $P_i$ returned by the second sensor is acquired; the data $P_{i+1}$ is acquired again when the jetted slurry at one time is uniformly stirred; the lifting height Z of the drill bit is recorded; the cement soil density is calculated by the single chip microprocessor according to the formula $\rho_{cement\ soil} = (P_{i+1} - P_i)/gZ$, wherein $g = 9.8\ g/cm^3$; and S3. Measured values are input to calculate the cement content: the cement slurry density $\rho_{cement\ slurry}$ obtained by calculation in step S1, the cement soil density $\rho_{cement\ soil}$ obtained by calculation in step S2, and the known data of water cement ratio and soil density are input into the input module; the cement content is calculated by the single chip microprocessor according to the formula cement content = $(\rho_{soil\ body} - \rho_{cement\ soil})\rho_{cement\ slurry}/[(1+\text{water cement ratio})(\rho_{cement\ soil} - \rho_{cement\ slurry})\rho_{soil\ body}]$, and then displayed on the second display module.

In the present invention, the cement content is calculated under the following assumptions:

(1) the volume of the cement soil after being hydrated keeps unchanged;

(2) the cement stirring pile body doesn't shrink after being molded and has already been uniformly stirred.

Thus, $$\rho_{cement\ soil} = (m_{cement\ slurry} + m_{soil\ body})/(m_{cement\ slurry}/\rho_{cement\ slurry} + m_{soil\ body}/\rho_{soil\ body}) \quad (a)$$

the calculation formula for the cement content in the cement soil can be derived from the formula (a):

$$\text{cement content} = \frac{m_{cement}}{m_{soil\,body}} = \frac{m_{cement\,slurry}}{1 + \text{water cement ratio}}$$

$$= \frac{(\rho_{soil\,body} - \rho_{cement\,soil})\rho_{cement\,slurry}}{(1 + \text{water cement ratio})}$$

$$(\rho_{cement\,soil} - \rho_{cement\,slurry})\rho_{soil\,body}$$

The present invention has the beneficial effects that the test system of the present invention can detect the cement slurry density and the cement soil density in real time at the construction site, so that the cement admixing amount can be detected in real time at the construction site during the foundation reinforcing process of the underground engineering, the traditional method for extracting a core sample on site and performing the measurement at the laboratory is abandoned, convenience and rapidness can be realized, the time period is short, the supervision effect is good, and the cheating on the workmanship and the materials can be effectively avoided.

Figure 1:
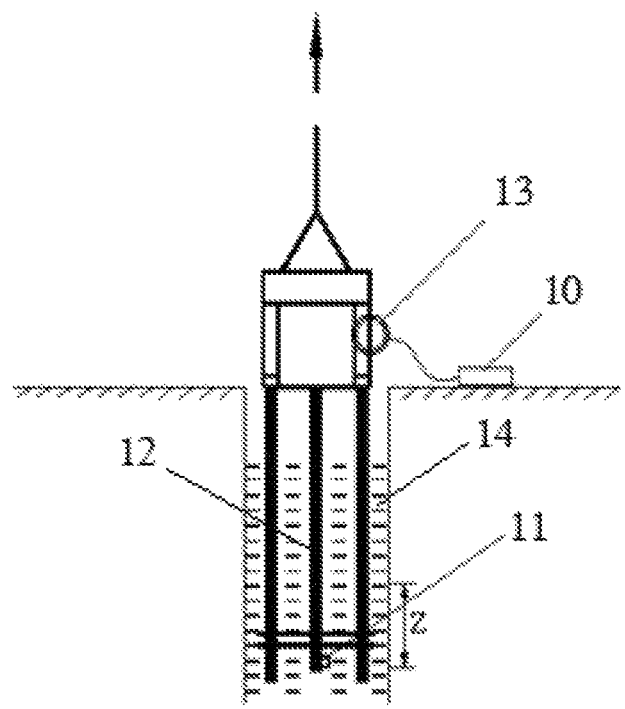
FIG. 1 is the schematic diagram illustrating the construction of the cement stirring pile body according to the present invention.

Meanings of the reference numerals in the drawings: 1: cement slurry tank; 2: first electric control center; 3: measuring wire; 4: gravity block; 5: first pressure sensor; 6: Power supply; 7: switch; 8: voltmeter; 9: resistor; 10: second electric control center; 11: second pressure sensor; 12: drill bit; 13: connecting coil; 11: cement stirring pile body.

DETAILED DESCRIPTION

The embodiments described below with reference to the drawings are exemplary and are intended to explain the present invention but not to limit the present invention. Ordinal numerals used in the claims and the specification such as "first", "second", "third", etc. are only used to modify the claims rather than containing any priority, precedence or representation of an order of one claim prior to another claim or a time sequence of executing steps of a method and are only served as a label to distinguish an element with a specified name of the claims from another element with the same name (rather than a term of the order).

The present invention is specifically illustrated below in combination with the drawings and specific embodiments.

Figure 2:
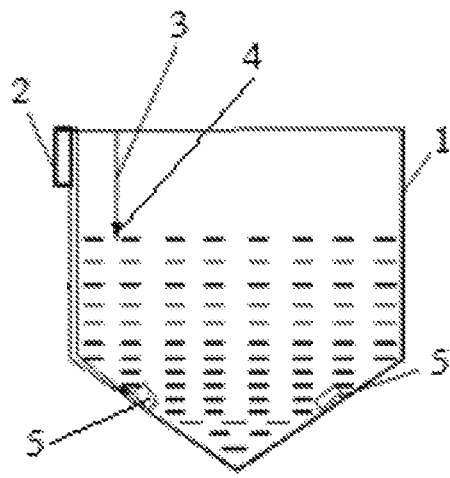
FIG. 2 is the schematic diagram illustrating the application of the cement slurry density measuring apparatus.

Referring to FIG. 1 and FIG. 2, the present invention first discloses a test system for detecting the cement content in a cement stirring pile body 14 in real time, and the test system specifically includes a cement slurry density measuring apparatus and a cement admixing amount calculating apparatus. The cement slurry density measuring apparatus may measure the density of the cement slurry, and specifically includes a first electric control center 2, a measuring wire 3 electrically connected with the first electric control center 2 and a plurality of first pressure sensors 5.

Figure 3:
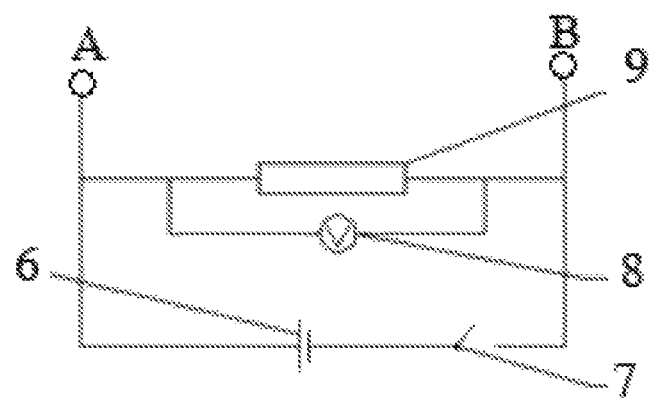
FIG. 3 is the structural schematic diagram illustrating the circuit structure of the first electric control center of the cement slurry density measuring apparatus in FIG. 2.

With reference to FIG. 3, the first electric control center 2 includes a power supply 6, a switch 7, a voltmeter 8, a resistor 9, a data processing module and a first display module, wherein when the measuring wire 3 perpendicularly drops to contact with the liquid surface of the cement slurry from the top of the cement slurry tank 1, two ends A and B of the circuit of the first electric control center in FIG. 3 are switched on, and the numerical value of the voltmeter 8 is changed (suddenly changed). Further, as shown in FIG. 2, the end portion of the measuring wire 3 is provided with a gravity block 4, thus it can ensure the vertical dropping of the wire 3 from the top of the cement slurry tank 1, so that to ensure the reliability of the test result. The first pressure sensors 5 are arranged at the bottom of the cement slurry tank the pressure test data is then fed back to the data processing module, and the cement slurry density is calculated and then displayed on the first display module. In order to improve the measuring accuracy, the number of the first pressure sensors 5 is 2, 4 or 6, the first pressure sensors are uniformly distributed on the bottom wall of the cement slurry tank 1, and the pressure numerical value of the cement slurry is obtained by means of calculating an average value.

The cement admixing amount calculating apparatus may implement the measurement of the cement soil density and the calculation of the cement content, and specifically includes a second electric control center 10 and a second pressure sensor 11 electrically connected with the second electric control center 10, wherein the second pressure sensor 11 is fixed at the end portion of the drill bit 12, and the drill bit 12 stretches into the pile body to be tested; the second electric control center 10 includes a data acquisition module, a single chip microprocessor, a second display module and an input module; data acquired by the second sensor is fed back to the data acquisition module, and the cement soil density is calculated by the single chip microprocessor and displayed on the second display module; and the cement slurry density, the cement soil density, water cement ratio and the soil density are input into the input module, and the cement content is calculated by the single chip microprocessor and displayed on the second display module.

It should be noted that the connecting coil 13 between the second electric control center 10 and the second pressure sensor 11 should be long enough so as to facilitate the remote operation, thereby improving the safety.

In order to better understand the present invention, the test method for detecting the cement content of the cement stirring pile body 14 in real time with the test system is described in detail. It is assumed that the volume of the cement soil after being hydrated keeps unchanged, the cement stirring pile body doesn't shrink after being molded, and the cement stirring pile body has already been uniformly stirred.

The method specifically includes the following steps:

S1. the density of the cement slurry in the cement slurry tank 1 is measured: the switch 7 of the first electric control center 2 is closed; the numerical value of the voltmeter 8 is essentially constant at the moment; the measuring wire 3 is vertically and slowly dropped from the top of the cement slurry tank 1; when the reading of the voltmeter 8 changes, it indicates that the measuring wire 3 contacts with the liquid surface of the cement slurry; the length h of the measuring wire 3 and the height H of the cement slurry tank 1 are measured; the return value P of the first pressure sensors 5 is recorded; the cement slurry density is calculated according to the formula $\rho_{cement\,slurry} = P/g(H-h)$, wherein $g = 9.8$ g/cm$^3$, h is the height from the top of the cement slurry tank 1 to the liquid surface of the cement slurry, and H is the total height of the cement slurry tank 1; and if there are multiple first pressure sensors 5, the average value $\overline{P}$ is calculated so as to improve the reliability of the measurement result;

S2. the cement soil density is measured: a stress measuring signal is transmitted by the second electric control center 10; data $P_i$ returned by the second sensor is acquired; data $P_{i+1}$ is acquired again when the sprayed slurry is uniformly stirred; the lifting height Z of the drill bit 12 is recorded; and the cement soil density is calculated by the single chip microprocessor according to the formula $\rho_{cement\ soil}=(P_{i+1}-P_i)/gZ$, wherein g=9.8 g/cm$^3$; and S3. the measured values are input to calculate the cement content: the cement slurry density $\rho_{cement\ slurry}$ obtained by calculation in step S1, the cement soil density $\rho_{cement\ soil}$ obtained by calculation in step S2, and known data provided in an engineering report such as water cement ratio and soil density are input into the input module, and the cement content is calculated by the single chip microprocessor according to the formula cement content= $(\rho_{soil\ body}-\rho_{cement\ soil})\rho_{cement\ slurry}/[(1+\text{water cement ratio})(\rho_{cement\ soil}-\rho_{cement\ slurry})\rho_{soil\ body}]$, and displayed on the second display module.

To sum up, the present invention has the beneficial effects that the test system of the present invention can detect the cement slurry density and the cement soil density in real time at the construction site, so that the cement admixing amount can be detected in real time at the construction site during the foundation reinforcing process of the underground engineering; convenience and rapidness can be realized; the time period is short; the supervision effect is good; and the cheating on the workmanship and the materials can be effectively avoided.

The basic principle, main characteristics and advantages of the present invention are shown and described above. Those skilled in the art should appreciate that the foregoing embodiments do not limit the present invention in any way; and any technical solution obtained by adopting a way of equivalent replacements or equivalent transformations shall fall within the protection scope of the present invention.

What is claimed is:

1. A test system for detecting cement content of a cement stirring pile body m real time, comprising a cement slurry density measuring apparatus and a cement admixing amount calculating apparatus, wherein,
   the cement slurry density measuring apparatus comprises a first electric control center, a measuring wire electrically connected with the first electric control center and a plurality of first pressure sensors; the first electric control center comprises a power supply, a switch, a voltmeter, a resistor, a data processing module and a first display module; when the measuring wire perpendicularly drops to contact with a cement slurry liquid surface from a top of a cement slurry tank, a numerical value of the voltmeter changes; the first pressure sensors are arranged at a bottom wall of the cement slurry tank, and a pressure test data is fed back to the data processing module, and a cement slurry density is calculated and then displayed on the first display module; and
   the cement admixing amount calculating apparatus comprises a second electric control center and a second pressure sensor electrically connected with the second electric control center, the second pressure sensor is fixed at an end portion of, a drill bit, and the drill bit stretches into the pile body to be tested; the second electric control center comprises a data acquisition module, a single chip microprocessor, a second display module and an input module, and when data acquired by the second pressure sensor is fed bask to the data acquisition module, a cement soil density is calculated by the single chip microprocessor and then displayed on the second display module; and the cement slurry density, the cement soil density, a water cement ratio and soil density are inputted into the input module, and then the cement content is calculated by the single chip microprocessor and displayed on the second display module.

2. The test system for detecting cement content of a cement stirring pile body in real time according to claim 1, wherein,
   the number of the first pressure sensors is 2, 4 or 6, and the first pressure sensors are uniformly distributed on the bottom wall of the cement slurry tank.

3. The test system for detecting cement content of a cement stirring pile body in real time according to claim 1, wherein,
   an end portion of the measuring wire is provided with a gravity block.

4. A test method for detecting cement content of a cement stirring pile body in real time using a test system,
   the method comprises the following steps:
      wherein, the test system comprises a cement slurry density measuring apparatus and a cement admixing amount calculating apparatus,
      the cement slurry density measuring apparatus comprises a first electric control center, a measuring wire electrically connected with the first electric control center and a plurality of first pressure sensors; the first electric control center comprises a power supply, a switch, a voltmeter, a resistor, a data processing module and a first display module; when the measuring wire perpendicularly drops to contact with a cement slurry liquid surface from a top of a cement slurry tank, a numerical value of the voltmeter changes; the first pressure sensors are arranged at a bottom wall of the cement slurry tank, and a pressure test data is fed back to the data processing module, and a cement slurry density is calculated and then displayed on the first display module; and
      the cement admixing amount calculating apparatus comprises a second electric control center and a second pressure sensor electrically connected with the second electric control center, the second pressure sensor is fixed at an end portion of a drill bit, and the drill bit stretches into the pile body to be tested; the second electric control center comprises a data acquisition module, a single chip microprocessor, a second display module and an input module, and when data acquired by the second pressure sensor is fed back to the data acquisition module, a cement soil density is calculated by the single chip microprocessor and then displayed on the second display module; aid the cement slurry density, the cement soil density, a water cement ratio and soil density are inputted into the input module, and then the cement content is calculated by the single chip microprocessor and displayed on the second display module,
      S1. measuring the cement slurry density in the cement slurry tank, wherein, switch of the first electric control center is closed; the measuring wire is vertically dropped from the top of the cement slurry tank; the measuring wire contacts with the liquid surface of the cement slurry when a reading of the voltmeter changes; a length h of the measuring wire and a height H of the cement slurry tank are measured; a return value P of each first pressure sensor is recorded; and the cement slurry density is calculated by the data processing module according to a formula $\rho_{cement\ slurry}=P/g(H-h)$, wherein $g=9.8$ g/cm³;

S2. measuring the cement soil density, wherein, a stress measuring signal is transmitted by the second electric control center; data $P_i$ outputted by the second pressure sensor is acquired; data $P_{i+1}$ is obtained again when jetted slurry at one time is uniformly stirred; a lifting height Z of the drill bit is recorded; the cement soil, density is calculated by the single chip microprocessor according to a formula $\rho_{cement\ soil}=(P_{i+1}-P_i)/gZ$, wherein $g=9.8$ g/cm³; and S3. inputting the measured values to calculate the cement content, wherein, the cement slurry density $\rho_{cement\ slurry}$ obtained in step S1, the cement soil density $\rho_{cement\ soil}$ obtained in step S2, and data of a water cement ratio and a soil density are inputted into the input module; the cement content is calculated by the single chip microprocessor according to a formula:

cement content=$(\rho_{soil\ body}-\rho_{cement\ soil})\rho_{cement\ slurry}/[(1+$ water cement ratio$)(\rho_{cement\ soil}-\rho_{cement\ slurry})\rho_{soil\ body}]$, and then displayed on the second display module.

5. The test method for detecting cement content of a cement stirring pile body in real time according to claim 4, wherein, the number of the first pressure sensors is 2, 4 or 6, and the first pressure sensors are uniformly distributed on the bottom wall of the cement slurry tank.

6. The test method for detecting cement content of a cement stirring pile body in real time according to claim 4, wherein, an end portion of the measuring wire is provided with a gravity block.

* * * * *